US011298296B1

(12) United States Patent
Feldman et al.

(10) Patent No.: US 11,298,296 B1
(45) Date of Patent: Apr. 12, 2022

(54) MEDICATION VENDING DEVICE WITH VERIFICATION THAT MEDICATIONS LOADED THEREIN MATCH CURRENT PRESCRIPTION

(71) Applicant: Medherent, LLC, Annapolis, MD (US)

(72) Inventors: Joel F. Feldman, Owings Mills, MD (US); Yeardley W. Green, Stevenson, MD (US)

(73) Assignee: MEDHERENT, LLC, Annapolis, MD (US)

( * ) Notice: Subject to any disclaimer, the term of this patent is extended or adjusted under 35 U.S.C. 154(b) by 0 days.

(21) Appl. No.: 17/116,308

(22) Filed: Dec. 9, 2020

(51) Int. Cl.
*A61J 7/04* (2006.01)
*G16H 20/13* (2018.01)
*G16H 40/67* (2018.01)

(52) U.S. Cl.
CPC .......... *A61J 7/0481* (2013.01); *A61J 7/0418* (2015.05); *G16H 20/13* (2018.01); *G16H 40/67* (2018.01); *A61J 2200/30* (2013.01); *A61J 2205/10* (2013.01)

(58) Field of Classification Search
CPC .... A61J 7/0481; A61J 7/0418; A61J 2205/10; A61J 2205/30; A61J 2200/30; G16H 20/13; G16H 40/67
See application file for complete search history.

(56) References Cited

U.S. PATENT DOCUMENTS

| | | | |
|---|---|---|---|
| 4,847,764 A | 7/1989 | Halvorson | |
| 5,710,551 A * | 1/1998 | Ridgeway | ............. A61J 7/0481 340/870.09 |
| 6,505,095 B1 | 1/2003 | Kolls | |
| 6,594,549 B2 | 7/2003 | Siegel | |
| 6,766,219 B1 | 7/2004 | Hasey | |
| 7,069,226 B1 | 6/2006 | Kleinfelter | |
| 7,264,136 B2 | 9/2007 | Willoughby et al. | |
| 7,574,377 B2 | 8/2009 | Carapelli | |
| 7,612,662 B2 * | 11/2009 | Niemiec | ................ G16H 40/67 340/539.12 |
| 7,706,915 B2 | 4/2010 | Mohapatra et al. | |
| 7,963,201 B2 | 6/2011 | Willoughby et al. | |

(Continued)

OTHER PUBLICATIONS

"Data Transfer Standard EVA DTS 6.1." European Vending Association, Apr. 2008, 16 pages.

(Continued)

*Primary Examiner* — Michael Collins
(74) *Attorney, Agent, or Firm* — Panitch Schwarze Belisario & Nadel LLP (57) ABSTRACT

A medication vending device is integrated into systems that ensure compliance with a medication dosing schedule of a patient. The medication vending device contains medication packages to be vended in accordance with the patient's dosing schedule. The system can check for prescription changes that occurred between the date of generation of the medication packages and the date of loading the medication packages into the medication vending device, and provide appropriate alert messages to inhibit loading of the medication packages into the medication vending device. In addition, post-loading prescription changes can be detected, and appropriate alert messages or actions can be taken regarding the medication packages currently loaded into the medication vending device.

22 Claims, 8 Drawing Sheets

(56) References Cited

U.S. PATENT DOCUMENTS

| | | | |
|---|---|---|---|
| 8,019,471 | B2 | 9/2011 | Bogash et al. |
| 8,027,748 | B2 | 9/2011 | Handfield et al. |
| 8,090,472 | B2 | 1/2012 | Schifman et al. |
| 8,196,774 | B1 | 6/2012 | Clarke et al. |
| 8,467,897 | B2 | 6/2013 | Holmes et al. |
| 8,757,435 | B2 | 6/2014 | Van Oort et al. |
| 8,983,654 | B2 | 3/2015 | Sugimoto |
| 9,117,010 | B2 | 8/2015 | Feldman et al. |
| 9,361,431 | B2 * | 6/2016 | Fauci ............... G07F 9/001 |
| 9,477,817 | B2 | 10/2016 | Feldman et al. |
| 2001/0025208 | A1 | 9/2001 | Bartur |
| 2005/0240305 | A1 * | 10/2005 | Bogash ............... G07F 11/68 700/242 |
| 2006/0200369 | A1 | 9/2006 | Batch et al. |
| 2009/0167531 | A1 | 7/2009 | Ferguson |
| 2009/0259486 | A1 | 10/2009 | Burg et al. |
| 2010/0114367 | A1 | 5/2010 | Barrett et al. |
| 2010/0168904 | A1 | 7/2010 | Henderson et al. |
| 2010/0305975 | A1 | 12/2010 | Daya et al. |
| 2010/0324936 | A1 | 12/2010 | Vishnubhatla et al. |
| 2011/0000170 | A1 | 1/2011 | Burg et al. |
| 2011/0202174 | A1 | 8/2011 | Bogash et al. |
| 2011/0251850 | A1 | 10/2011 | Stephens |
| 2015/0019009 | A1 | 1/2015 | Feldman et al. |
| 2015/0058041 | A1 * | 2/2015 | Ervin ............... G16H 10/60 705/3 |
| 2017/0109497 | A1 * | 4/2017 | Tribble ............... G06F 16/9535 |
| 2017/0169185 | A1 * | 6/2017 | Weng ............... G16H 80/00 |

OTHER PUBLICATIONS

"EVA Data Transfer Standard." European Vending Association, printout from web page: http://www.vending-europe.eu/_includes/print.php?lg=en&cmp_id=17&safe_mode=, printout date: Feb. 29, 2012, original posting date: unknown, 3 pages.

"Notification of Transmittal of The International Search Report and The Written Opinion of the International Searching Authority . . . " and corresponding "Search History" document for PCT/US14/30316, dated Mar. 16, 2015, 26 pages.

Brochure for PointClickCare eMAR system. Printout from web page: https://www.pointclickcare.com/pccwebsite/pdfs/eMar_VicVillage.pdf, 2008, 2 pages.

Extended European Search Report dated Oct. 21, 2016 in EP Application No. 14765513.8.

Gene Ostendorf, "DEX and MDB: A Primer for Vendors." printout from web page: http://www.vendingmarketwatch.com/article/10272928/dex-and-mdb-a-primer-for-vendors, Feb. 7, 2008, 5 pages.

International Preliminary Report on Patentability for PCT/US14/30316, dated Sep. 24, 2015, 12 pages.

JuGeon Pak and KeeHyun Park. "Construction of a smart medication dispenser with a high degree of scalability and remote manageability." Journal of Biomedicine and Biotechnology, 2012, 10 pages.

Karla Miller et al. "Evaluation of medications removed from automated dispensing machines using the override function leading to multiple system changes," printout from web page: http://www.ahrq.gov/downloads/pub/advances2/vol4/Advances-Miller_93.pdf, original publication date: 2008 (as per Internet Archive Wayback Machine records), 7 pages.

Michael L. Kasavana and Glenn Butler, "Vending Technology Revolution." printout from web page: http://www.vending.org/technology/Vending_Technology_Revolution.pdf, original publication date: 2010 (as per Internet Archive Wayback Machine records), 11 pages.

Office Action dated Aug. 11, 2016 in Canadian Patent Application No. 2,906,161, 8 pages.

Office Action dated Feb. 9, 2017 in Canadian Patent Application No. 2,906,161, 8 pages.

Office Action dated Aug. 8, 2017 in CA Application No. 2,906,161.

PCT Invitation to Pay Additional Fees and Where Applicable, Protest Fees for PCT/US14/30316 dated Jan. 15, 2015, 3 pages.

Product brochure for "MedSupport® for Providers." CaraSolva, Inc., Boulder, Colorado, 2011, 2 pages.

Product brochure for "MedSupport®." CaraSolva, Inc., Boulder, Colorado, 2011, 2 pages.

Product brochure for "PharmacySupport." CaraSolva, Inc., Boulder, Colorado, 2011, 2 pages.

Rajeev B. Patel, "Reduction in Medication Errors in Hospitals." printout from web page: http://www.cwru.edu/med/epidbio/mphp439/Reduction%20in%20Medication%20Errors%20in%20Hospitals.htm, Spring 2004, 11 pages.

Wikipedia entry for "Health Level 7." printout from: http://en.wikipedia.org/wiki/Health_Level_7, last modified date Dec. 28, 2011, 11 pages.

Wikipedia entry for "Medication Administration Record." printout from web page: http://en.wikipedia.org/wiki/Medication_Administration_Record, last modified date: Dec. 23, 2011, 2 pages.

* cited by examiner

| patient identifier | patient dosing schedule |
|---|---|
| 1234 | |
| ... | ... |
| 5678 | |
| ... | ... | memory 62
patient dosing schedule 64

Fig. 1C

| IP address | Contents of Slot 1 (COL 1) | Contents of Slot 2 (COL 2) | Contents of Slot 3 (COL 3) |
|---|---|---|---|
| ABCDEF | 1 pill of MEDICINE A<br>1 pill of MEDICINE B<br>2 pills of MEDICINE C | 1 pill of MEDICINE D<br>1 pill of MEDICINE E | 1 pill of MEDICINE A<br>1 pill of MEDICINE B<br>2 pills of MEDICINE C |
| GHIJKL | 1 pill of MEDICINE M<br>2 pills of MEDICINE N | 1 pill of MEDICINE O<br>1 pill of MEDICINE P<br>1 pill of MEDICINE Q | 1 pill of MEDICINE M<br>2 pills of MEDICINE N |

Order ID table 69

| Order Fill Date | Order ID | Patient identifier | Contents of medication packages (each letter represents a specific medication and dose amount of the medication) |
|---|---|---|---|
| 10-25-2020 | 1234567890 | 1234 | 8:00 am: X, Y, Z   12:00 noon: X, Y   8:00 pm: Y, Z |
| 10-25-2020 | 1234567895 | 5678 | 8:00 am: A, B, C   12:00 noon: A, B, C   8:00 pm: A, B, D |
| ⋮ | ⋮ | ⋮ | ⋮ |
| 10-28-2020 | 1234569001 | 1234 | 8:00 am: X, Y, W   12:00 noon: X, Y   8:00 pm: Y, W |

Fig. 1E

Order ID table 69'

| Order Fill Date | Order ID | Patient identifier | Contents of medication packages (each letter represents a specific medication and dose amount of the medication) |
|---|---|---|---|
| 10-25-2020 | 1234567890 | 1234 | 8:00 am: X, Y, Z |
| 10-25-2020 | 1234567891 | 1234 | 12:00 noon: X, Y |
| 10-25-2020 | 1234567892 | 1234 | 8:00 pm: Y, Z |
| 10-25-2020 | 1234567895 | 5678 | 8:00 am: A, B, C |
| 10-25-2020 | 1234567896 | 5678 | 12:00 noon: A, B, C |
| 10-25-2020 | 1234567897 | 5678 | 8:00 pm: A, B, D |
| ⋮ | ⋮ | ⋮ | ⋮ |
| 10-28-2020 | 1234569001 | 1234 | 8:00 am: X, Y, W |
| 10-28-2020 | 1234569003 | 1234 | 8:00 pm: Y, W |

(Prior Art)

MEDICATION VENDING DEVICE WITH VERIFICATION THAT MEDICATIONS LOADED THEREIN MATCH CURRENT PRESCRIPTION

BACKGROUND OF THE INVENTION

Medication vending or dispensing devices (collectively referred to hereafter as "medication vending devices") vend medications in accordance with a preprogrammed medication dosing schedule. Medication dosing schedules indicate which medications should be taken at different dose times of the day. Dosing schedules are typically the same each day, but some dosing schedules may require multiple days to define a proper schedule, especially when a particular medication is not taken every day of a given week, or is taken at different dose levels or does times on different days of a given week. The patient's physician may periodically change a patient's dosing schedule by adding or deleting medications, or changing the dose amount or dose frequency of a particular medication.

One type of medication vending device outputs a prompt when a dosing time occurs. The prompt indicates that the patient should take action to cause the medication vending device to release the appropriate medication therefrom which is associated with the current dose time so that the medication can be immediately consumed. In some cases, a PIN must be entered by the patient or a caregiver to complete the vending process. One example of this type of medication vending device is described in U.S. Pat. No. 9,117,010 (Feldman et al.), which is incorporated by reference herein.

Another type of medication vending device is automatically programmed to vend all medication doses at their respective scheduled dose times, without requiring any patient action. Such devices may also prompt the patient to immediately consume the vended medication.

Medication vending devices such as the device described in U.S. Pat. No. 9,117,010 are filled with medications as follows:

1. At periodic intervals, such as once per month, the patient's most current dosing schedule is retrieved from a data repository, such as an electronic pharmacy server, and medication packages are prepared at a pharmacy dispensing location, which may be a retail location, or a non-retail pharmacy fulfillment location which may employ robotic equipment to create the medication packages.

2. The medication packages are physically delivered to the location of the medication vending device, which may the patient's residence, and are loaded into the medication vending device.

3. To ensure that the medication packages reflect the most current dosing schedule, the medication packages are typically prepared very shortly before they are to be loaded into the medication vending device. For example, if the medication vending device is refilled monthly, the medication packages may be prepared a week prior to the new monthly cycle, which provides sufficient time to prepare the medication packages and deliver them to the medication vending device before the previous month's supply runs out.

Despite the short time frame between creation of the medication packages and loading of the medication packages into a medication vending device, it may still be possible that the patient's prescription may have changed during that time frame. In addition, the patient's prescription may also change after the medication packages have been loaded into a medication vending device, such as during the monthly cycle of the currently loaded medication packages. Neither of these scenarios are sufficiently addressed by the automated vending process described in U.S. Pat. No. 9,117,010. Thus, there is a need for a medication vending device that can address these scenarios. The present invention fulfills such a need.

SUMMARY OF THE PRESENT INVENTION

A medication vending device is integrated into systems that ensure compliance with a medication dosing schedule of a patient. The medication vending device contains medication packages to be vended in accordance with the patient's dosing schedule. The system can check for prescription changes that occurred between the date of generation of the medication packages and the date of loading the medication packages into the medication vending device, and provide appropriate alert messages to inhibit loading of the medication packages into the medication vending device. In addition, post-loading prescription changes can be detected, and appropriate alert messages or actions can be taken regarding the medication packages currently loaded into the medication vending device.

BRIEF DESCRIPTION OF THE DRAWINGS

Preferred embodiments of the present invention will now be described by way of example with reference to the accompanying drawings.

DETAILED DESCRIPTION OF THE INVENTION

Certain terminology is used herein for convenience only and is not to be taken as a limitation on the present invention.

The words "a" and "an", as used in the claims and in the corresponding portions of the specification, mean "at least one."

The present invention may be used to track the ingestion/administering/vending of single medicine packages or Multi-Unit Dose Packages or Multi-Unit Drug Packages (MUDPs). An MUDP contains one dosage of medicines that are prescribed for a specific treatment regimen. That is, there are a plurality of different medicines in an MUDP, and there may be one or pills of each medicine to obtain the desired dosage. All of the different medications in an MUDP packet are meant to be taken at the same time. MUDPs are typically created using specialized robotic machinery. However, the scope of the present invention includes MUDPs that are manually packaged in simple plastic packets or the like.

An MUDP typically includes a label that describes its contents, or it may include human or machine readable indicia (e.g., an ID number) that functions as a pointer in a database memory that stores its contents. The label may also include patient identifying information. The machine readable indicia may be a bar code or QR code that identifies the patient, date, and medication. The examples described below relate to MUDPs, but the scope of the present invention includes single medicines or packages that include only one medicine type per package.

Dispensing vs. vending: As discussed in U.S. Pat. No. 9,117,010, there are two steps involved in the medication lifecycle. The first step in the lifecycle is a dispensing step which occurs when a pharmacist or similarly qualified individual fills a medication vending device, such as the one described in the present invention, with prescribed medications. This step is conventionally referred to as "medication dispensing," wherein specific medication(s) are delivered to a patient in fulfillment of a prescription. Typically, the medications are physically handed to the patient, but in the present invention, the medications are loaded into the medication vending device, thereby completing the dispensing step. The second step in the lifecycle is a vending step wherein the medication vending device releases the previously dispensed medications to the patient. In a conventional vending machine, the release of a product from a vending machine is typically referred to as a dispensing event, but in the context of the present invention, it is referred to as a vending event, because the dispensing event occurred when the medication vending device was loaded with the medications. While dispensing and vending are different steps in the medication lifecycle, the discussion below uses these terms interchangeably. Thus, for purposes of the present invention, all references below to "dispensing" and permutations thereof are deemed to be equivalent to the act of "vending" (a vending event).

Between the first and second steps of the medication lifecycle, additional actions (intermediary steps) occur. One intermediary step is that the dispensed medications are provided to a technician who physically loads the medications into the medication vending device. Another intermediary step is that the dispensed medications are packaged into single medicine packages or MUDPs, as discussed above. The packaging occurs prior to the step of the technician loading the medication vending device.

Dosing schedule: A patient's dosing schedule is similar to the dose schedule shown for Patient ID 1234 in FIG. 43 of U.S. Pat. No. 9,117,010, repeated below for convenience.

TABLE 1

| Dosing schedule | Dispensed meds (meds that are scheduled to be dispensed and which were previously placed in the vending machine) |
| --- | --- |
| 8:00 am | 1 pill of MEDICINE A |
|  | 1 pill of MEDICINE B |
|  | 2 pills of MEDICINE C |
| 12:00 noon | 1 pill of MEDICINE D |
|  | 1 pill of MEDICINE E |
| 8:00 pm | 1 pill of MEDICINE A |
|  | 1 pill of MEDICINE B |
|  | 2 pills of MEDICINE C |

In this example, the medications are vended in multi-unit dose packages (MUDPs). Thus, a single package contains all of the medications vended at a respective dose time. This example relates to MUDPs, but the scope of the present invention includes single non-packaged medicines, or packages that include only one medicine type per package.

Figure 1A:
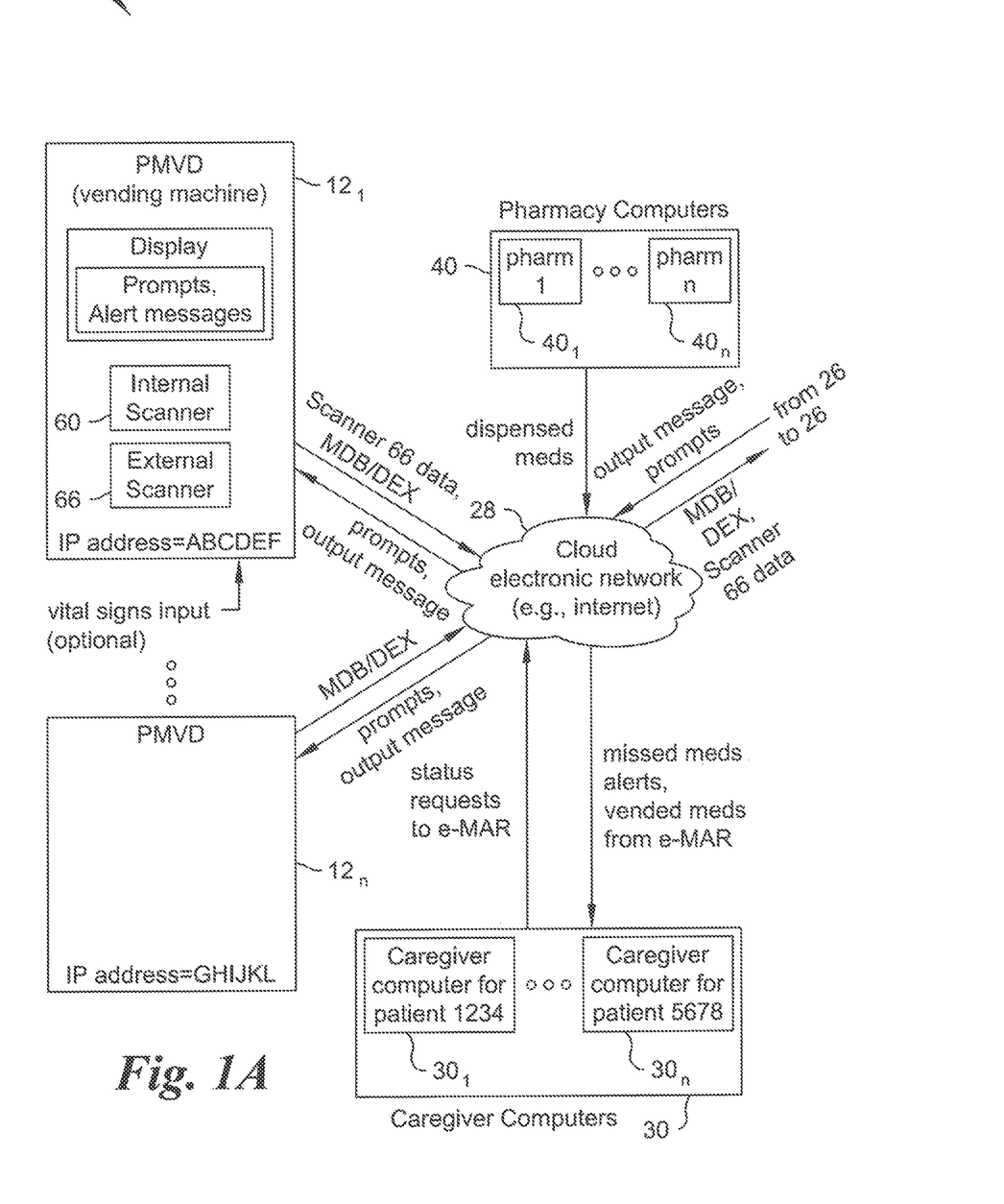
FIGS. 1A-1F, taken together, is a schematic diagram of a system that integrates a medication vending device therein, in accordance with one preferred embodiment of the present invention.
Figure 1B:
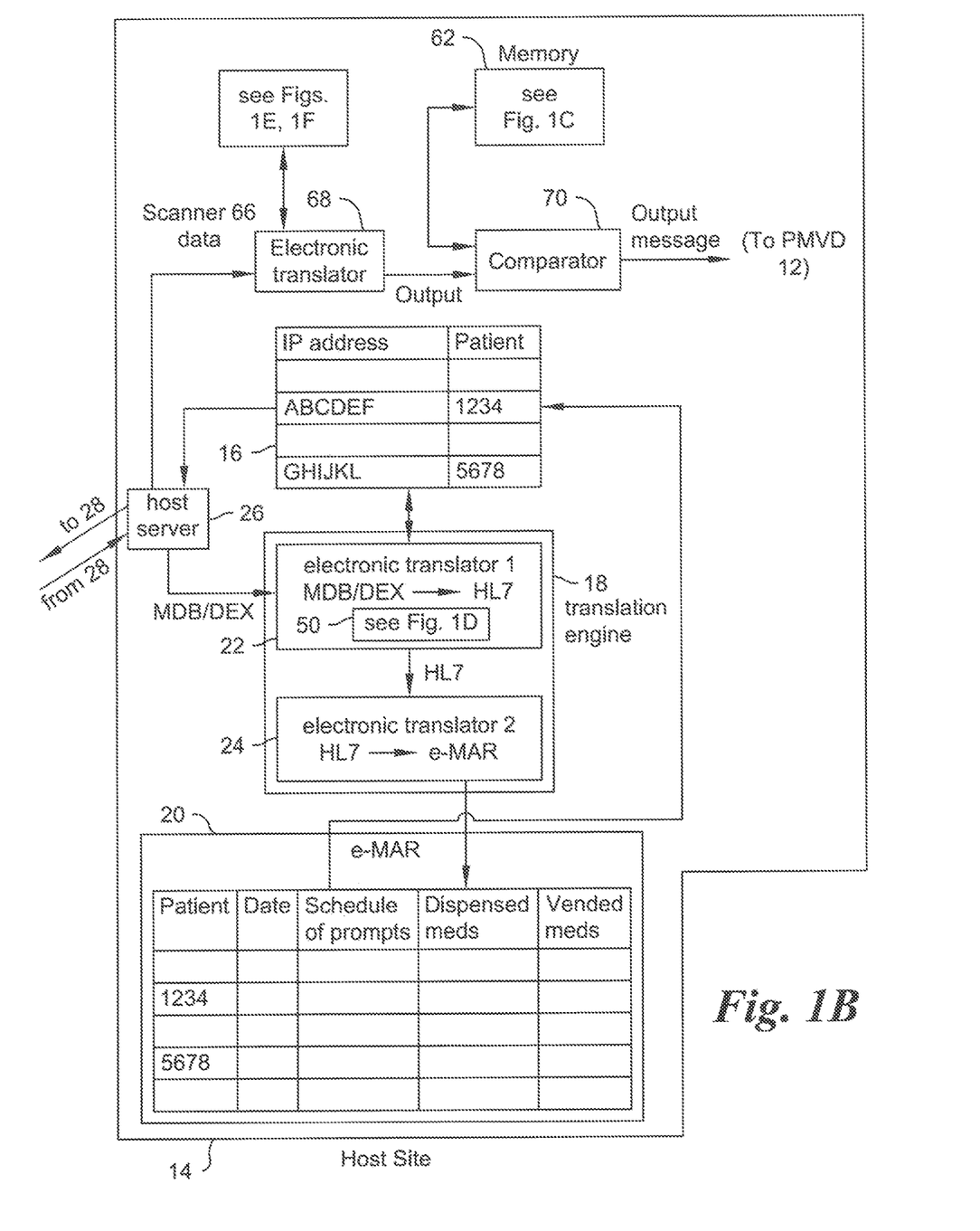

FIGS. 1A and 1B, taken together, is a schematic diagram of a system (apparatus) 10 in accordance with one preferred embodiment of the present invention. The system 10 includes a plurality of medication vending devices 12 (the internal elements of only one such device 12 is shown in FIG. 1A), a plurality of pharmacy computers 40, a plurality of caregiver computers 30, a host site 14, and an electronic network 28 for providing electronic communications among the above-identified elements. The host site 14, which includes host server 26, is also interchangeably referred to herein as a "medication administration computer."

One example of a system 10 may be the system 10 described in U.S. Pat. No. 9,117,010 and illustrated in FIG. 1 of U.S. Pat. No. 9,117,010, enhanced with the features described below regarding medication dosing schedule compliance. Each medication vending device 10 is associated with a respective patient using any of the identifying techniques described in U.S. Pat. No. 9,117,010. The elements of system 10 of the present invention which are also shown in FIG. 1 of U.S. Pat. No. 9,117,010 are similar in operation to the corresponding elements in U.S. Pat. No. 9,117,010, and thus are not described in further detail herein, other than by being identified by element number as follows:

database 16
electronic translation engine 18
electronic medication administration record (e-MAR or eMAR) 20
first electronic translator 22
second electronic translator 24
database table 50

The preferred embodiments of the present invention may operate in parallel with the features of the system 10 described in U.S. Pat. No. 9,117,010, thereby enhancing the capabilities of this prior art system.

Features of the present invention which are not part of U.S. Pat. No. 9,117,010 are described next.

Figure 1C:
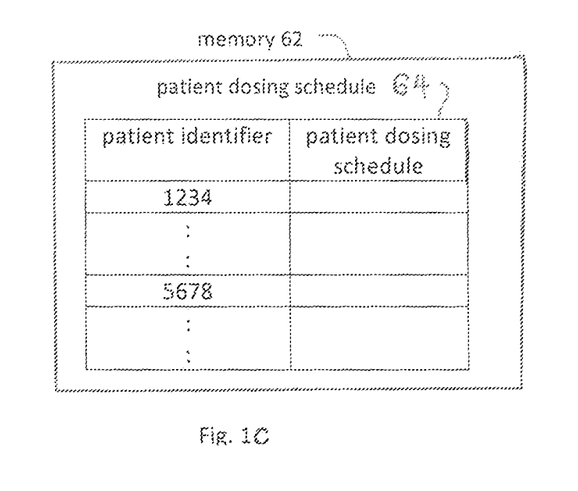
Figure 1D:
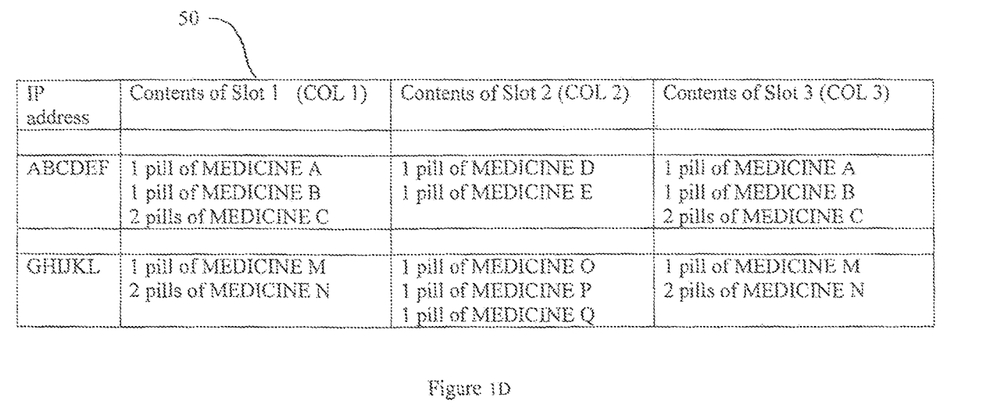

Referring to FIG. 1C, the system 10 includes memory 62 that stores a dosing schedule 64 for medication doses. The dosing schedule 64 may be loaded into the medication vending device 12 for use by the medication vending device 12 in vending medications, and may also be located in a remote location (i.e., remote from the medication vending device 12), such as in a dedicated server (not shown) dedicated to storing such data. Alternatively, the memory 62/dosing schedule 64 may be located in the host site 14, as shown in FIG. 1B. The dosing schedule includes (i) a plurality of dose (dosing) times per day, each day including a fixed number of dose times, and (ii) medications that are scheduled to be vended at each dose time. In yet another embodiment, the patient's dosing schedule 64 is stored in a remotely located server, and the memory 62 is located in the medication vending device 12. In this embodiment, the medication vending device 12 is in electronic communication with the remotely located server to allow the patient's dosing schedule 64 to be downloaded into the memory 62.

In one preferred embodiment of the present invention shown in FIG. 1A, the medication vending device 12 further includes an external scanner 66 that outputs scanner data, in addition to an internal scanner 60. The internal scanner 60 performs similar functions as the scanner 60 in U.S. Pat. No. 9,117,010, namely, reading a bar code or QR code printed on an MUDP as the MUDP is vended. The function of the external scanner 66 is described in more detail below. The display of the medication vending device 12 provides prompts, similar to the display in U.S. Pat. No. 9,117,010, but in this preferred embodiment, also provides alerts and alert messages, as further described below. The system 10 in the preferred embodiment shown in FIGS. 1A-1F of the present application further includes electronic translator 68 that receives and decodes the scanner data from the external scanner 66, optional order ID table 69, and comparator 70 that receives the output of the electronic translator 68 and data from the patient dosing schedule 64, and outputs a message regarding discrepancies identified in the comparator 70, which is electronically communicated to the medication vending device 12 for display, as further described below.

Referring again to FIG. 1A-1F of the present application, the system 10 provides an apparatus for ensuring compliance with a medication dosing schedule. The dosing schedule is associated with a specific patient and includes one or more dosing times per day. The medication is delivered to the patient via medication packages that are intended to match the dosing schedule. Each medication package includes a machine-readable code (e.g., a two-dimensional code, such as a QR code) printed thereon that is usable to identify at least (i) contents of the medication package, and (ii) a specific patient that the medication in the medication package was previously prescribed for.

Figure 2:
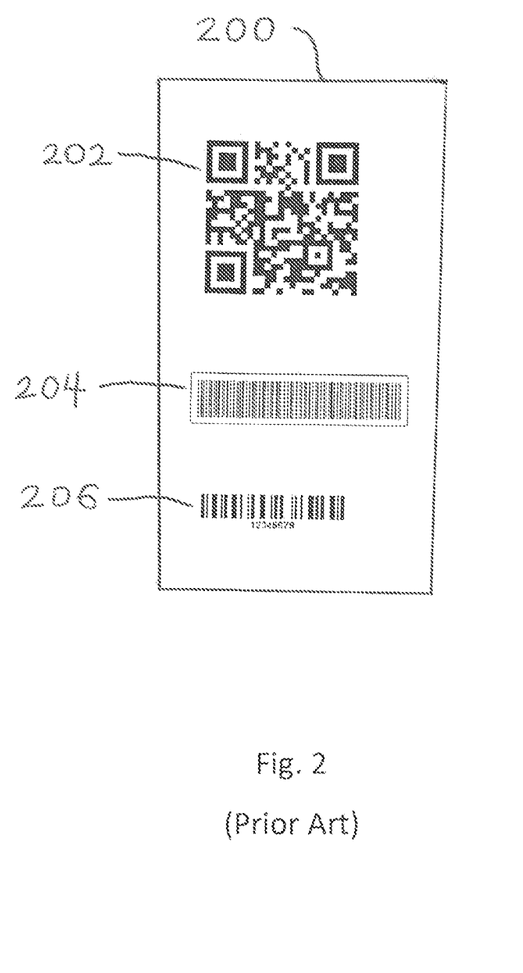
FIG. 2 is a prior art example of bar codes that can be printed on a medication package.

FIG. 2 is an example of a medication package 200 having multiple machine-readable codes printed on its outer packaging, including a two-dimensional (2-D) bar code 202, also referred to as a QR code, a long one-dimensional (1-D) bar code 204, and a short 1-D bar code 206. In this example, either the QR code 202 and the long 1-D bar code 204, when deciphered, indicates that the medication package contains the following medications (x, y, z) and belongs to patient (ABC), as discussed in more detail below. The short 1-D bar code 206 may be used to encode the dose time. In one preferred embodiment, the QR code 202 and the 1-D bar code 204 encode an order identifier (order ID), as discussed in more detail below. In an alternative embodiment, the machine-readable code does not directly indicate an order ID, but instead is usable to identify the order ID via a separate translation table (not shown) that stores each of the values represented by each generated machine-readable code that is placed on a medication package, and their respective order ID's, which, in turn, are located in an order ID table (discussed below).

As discussed above, the system 10 includes memory 62 that stores the patient's dosing schedule 64. The dosing schedule 64 includes a patient identifier. The system 10 further includes a plurality of medication vending devices $12_1$ to $12_n$, wherein each device is associated with a specific patient. Each medication vending devices 12 is configured to vend the medication packages previously loaded therein. The system 10 will be further described with respect to how a single the medication vending device $12_1$ (subsequently referred to as medication vending device 12) performs in the system 10.

The medication vending device 12 includes at least an identifier corresponding to a specific patient that the medication vending device 12 is assigned to, and an external scanner 66 configured to read the machine-readable code printed on selected ones of the medication packages prior to loading the medication packages into the medication vending device. For example, if loading is about to occur, one medication package for each daily dose (dosing) time is selected for scanning.

In one embodiment, the external scanner 66 is implemented using a combination of a camera and a scanner application (scanner app). More specifically, in this embodiment, the medication vending device 12 further includes an operating system (OS), one or more application software programs executed using the OS, wherein one of the application software programs is the scanner app, and a camera accessible by the scanner app.

As also discussed above, the system 10 further includes electronic translator 68 configured to receive and process the scanned machine-readable code that is outputted from the external scanner 66, and output at least the following data deciphered from the machine-readable code:

1. Contents of the scanned medication packages.
2. The specific patient that the medication in the medication packages was previously prescribed for.

Figure 1E:
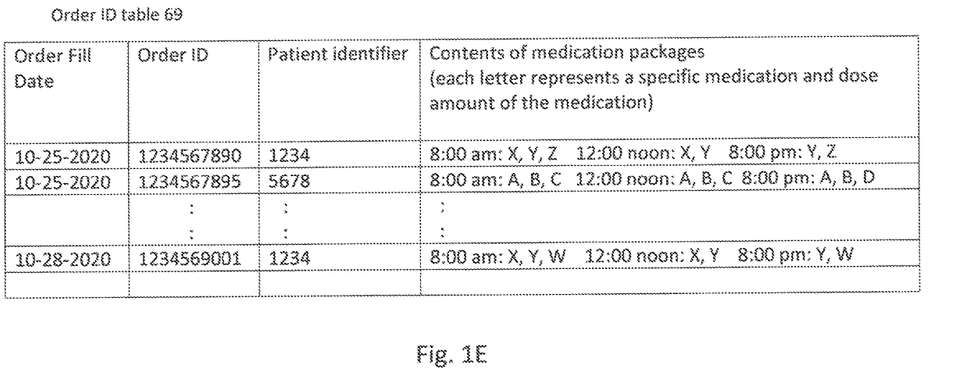

In one embodiment, the electronic translator 68 works in conjunction with order ID table 69 shown in FIG. 1E. In this embodiment, the contents of the scanned machine-readable code outputs an order ID, which is a numerical or alphanumeric value. This value is located in the order ID table 69 which maintains an entry for each order ID that indicates at least the contents of the scanned medication package, and the specific patient that the medication in the medication packages was previously prescribed for, as well as order fill date.

In an alternative embodiment, the contents of the scanned machine-readable code are more robust and directly encode data representing both the contents of the scanned medication packages and the specific patient that the medication in the medication packages was previously prescribed for. For example, some QR codes have the ability to encode sufficient data so as to capture all of this information. In this alternative embodiment, the order ID table 69 would not be necessary, and the electronic translator 68 merely uses the scanner 66 data to perform its function. However, for a QR code to encode sufficient data so as to capture all of this information, the QR code would need to have relatively large number of modules (squares), also referred to as "module density." (QR Codes are made of multiple rows and columns. The combination of these rows and columns makes a grid of modules (squares). There can be a maximum of 177 rows and 177 columns which means the maximum possible number of modules is 31,329. A QR code can thus store up to about 3 kB of data.) A QR code having a high module density requires a high-quality printer to produce the QR code, and also requires a high-quality (high resolution) scanner to read it. Assuming that these technical considerations are not cost-prohibitive, the QR codes may be used by themselves to encode sufficient data so as to capture all of the data that needs to be encoded, and thus avoid any need for the order ID table 69. However, in most cost-effective implementations, the QR code will not be able to capture all of the data that needs to be encoded, and the order ID table 69 will be used.

A one-dimensional (1-D) bar code would also typically not have sufficient data fields to capture such information, and thus the electronic translator 68 would also need to use the order ID table 69 to perform its function whenever a 1-D bar code is used.

As also discussed above, the system 10 further includes comparator 70 that is in electronic communication with the memory 62 that stores the patient's dosing schedule 64, and the medication vending device 12, and the output of the electronic translator 68. The comparator 70 may be part of the medication vending device 12, or it may be remote from the medication vending device, such as shown in FIG. 1B wherein the comparator 70 is located in the host site 14. The comparator 70 is configured to perform at least the following functions:

1. Compare the patient's dosing schedule 64 with the output of the electronic translator 68 to identify any discrepancies between (A) the patient's dosing schedule 64 and the contents of the scanned medication packages as outputted by the electronic translator 68, and (B) the patient identifier in the dosing schedule 64 and the specific patient that the medication in the scanned medication packages was previously prescribed for as outputted by the electronic translator 68.

2. Compare the identifier of the medication vending device 12 with one or more of (A) the specific patient that the medication in the scanned medication packages was previously prescribed for, and (B) the patient identifier in the dosing schedule 64. Preferably, one medication package is scanned for each dosing time per day, and the comparison is made between the dosing schedule 64 and the contents of the scanned medication packages for each of the daily dosing times.

3. Output a message indicating any discrepancies identified in the comparisons.

As noted above, the medication vending device 12 is in electronic communication with the comparator 70. This allows the medication vending device 12 to output the message indicating any discrepancies identified in the comparisons. The message provides an alert to either inhibit a person from loading selected ones of the medication packages into the medication vending device 12, or to communicate a change to the person so that the patient or the patient's caregiver may take appropriate action. In the latter example, the medication packages would still be loaded into the medication vending device 12.

Referring to the dosing schedule shown above in TABLE 1, examples of alert messages may include the following:

1. "Do not load 8:00 am dose." This message may be provided if any changes were made to the 8:00 am meds, such as discontinuing one of the meds, or changing the number of pills or dose amount of one of the medicines (e.g., MEDICINE C was changed from 2 pills to 1 pill; MEDICINE B was discontinued). The message may optionally indicate the reason for the change. Preferably, a new set of 8:00 am meds would be immediately prepared for immediate delivery to replace the outdated set of 8:00 am meds before the new monthly cycle begins.

2. "8:00 am dose of MEDICINE C was changed from 2 pills to 1 pill. Inform patient or patient's caregiver to discard 1 pill of MEDICINE C when taking each 8:00 am dose. In this scenario, the 8:00 am meds would still be loaded into the medication vending device 12.

In an alternative embodiment, the order ID and the order fill dates are used to determine whether to allow medication packages to be loaded, instead of the contents data. FIG. 1E illustrates this scenario. In preparation for the new month of filling a plurality of medication vending devices, a plurality of order ID's are generated for the patients on the 25th of the month (here, Oct. 25, 2020) and the medication packages are prepared based on the most current patient prescriptions. For example, order ID 1234567890 is generated for patient 1234. However, as known in the art, each time that a patient's prescription is modified, a new order ID is created, and a new batch of medication packages are generated for the patient. Here, order ID 1234569001 is generated for patient 1234 on Oct. 28, 2020 because there was a change to the medication given during the 8:00 am and 8:00 pm dose on that date, namely, that medication Z was changed to medication W. However, in this alternative embodiment, it is not necessary to know what medication(s) changed. Instead, the comparison process only uses the fact that a new order ID was generated for the patient ID associated with the medication vending device 12 being filled. Assuming that a patient's medication vending device 12 is being filled on the 29th, 30th, or 31st of Oct. 2020 with the medication packages created on Oct. 25, 2020 and which were already out for delivery to the medication vending device 12, the machine-readable code printed on the medication package identifies the order ID as 1234567890. This order ID is checked to determine if there are any subsequent order ID numbers for that patient (i.e., determine if the order ID is the most recent order ID). In this example, a subsequent order ID 1234569001 is detected. (The batch of medication packages associated with order ID 1234569001 may still be waiting for pickup at the dispensing location.) In this example, the medication vending device 12 generates an alert message not to load the medication packages. An optional message may be provided with specific information, such as to pick up a new batch of medication packages for subsequent loading into medication vending device 12 before the new month begins. Alternatively, the "no load" message may have a well-understood meaning to the person who loads the medication vending device 12 (e.g., an operator, a patient, or a patient's caregiver) that the batch being loaded does not contain the most currently prescribed medications, and thus should not be loaded. Continuing with this example, there is no subsequent order ID for patient 5678 (i.e., order ID 1234567895 is the most recent order for patient 5678), so when the comparison is performed at this patient's medication vending device 12, no such "no load" message is generated, and loading can proceed.

Referring to FIG. 1B, in this embodiment, the comparator 70 receives the decoded order ID from the scanner 66 data, and then compares it to the most recent order ID in FIG. 1E. If there is a match, loading can proceed. If there is not a match, then loading should not occur.

Figure 1F:
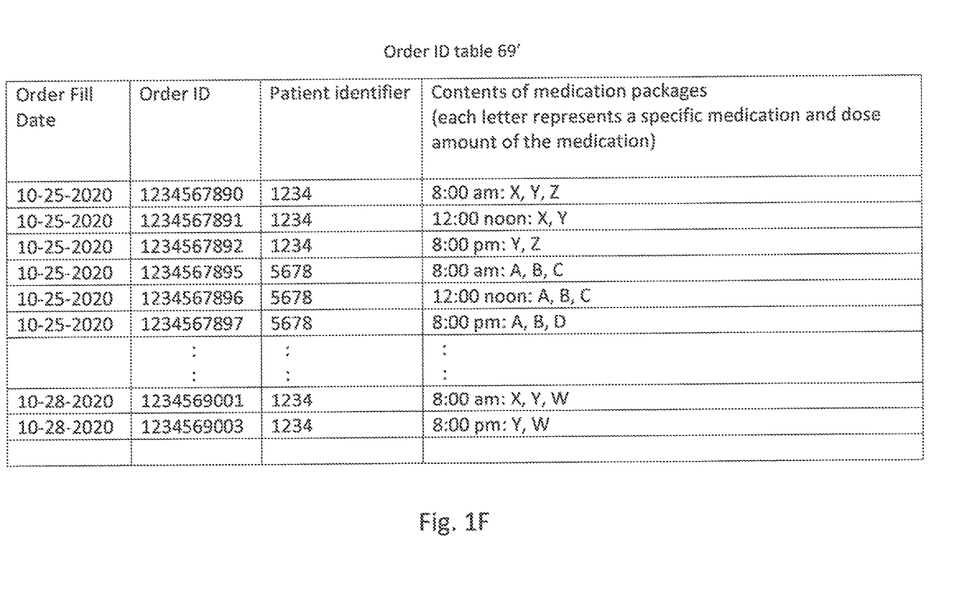

FIG. 1F shows order ID table 69' which is a minor variation of the order ID table 69'. In the order ID table 69', each dose time has its own order ID. In this embodiment, the medication packages are provided in three batches when there are three separate dose times. One medication package from each batch of dose times is scanned to capture its respective order ID, and then the same type of comparison is made as discussed above. One advantage of this embodiment is that if only one dose time has a medication change, the other dose times may be immediately loaded, and then it is only necessary to subsequently load new medication packages for the remaining dose times. In the example above, for patient 1234, the medication packages for the 12:00 noon dose can be immediately loaded because there was no new order ID for the medications in the 12:00 noon dose, whereas the 8:00 am and 8:00 pm medication packages must be replaced with the updated medication packages having the order IDs of 1234569001 and 1234569003, respectively.

Referring again to FIG. 1B, in this embodiment, the comparator 70 receives the decoded order ID from the scanner 66 data, and then compares it to the most recent order ID in FIG. 1F for the respective dose time. If there is a match, loading can proceed. If there is not a match, then loading should not occur.

Figure 3A:
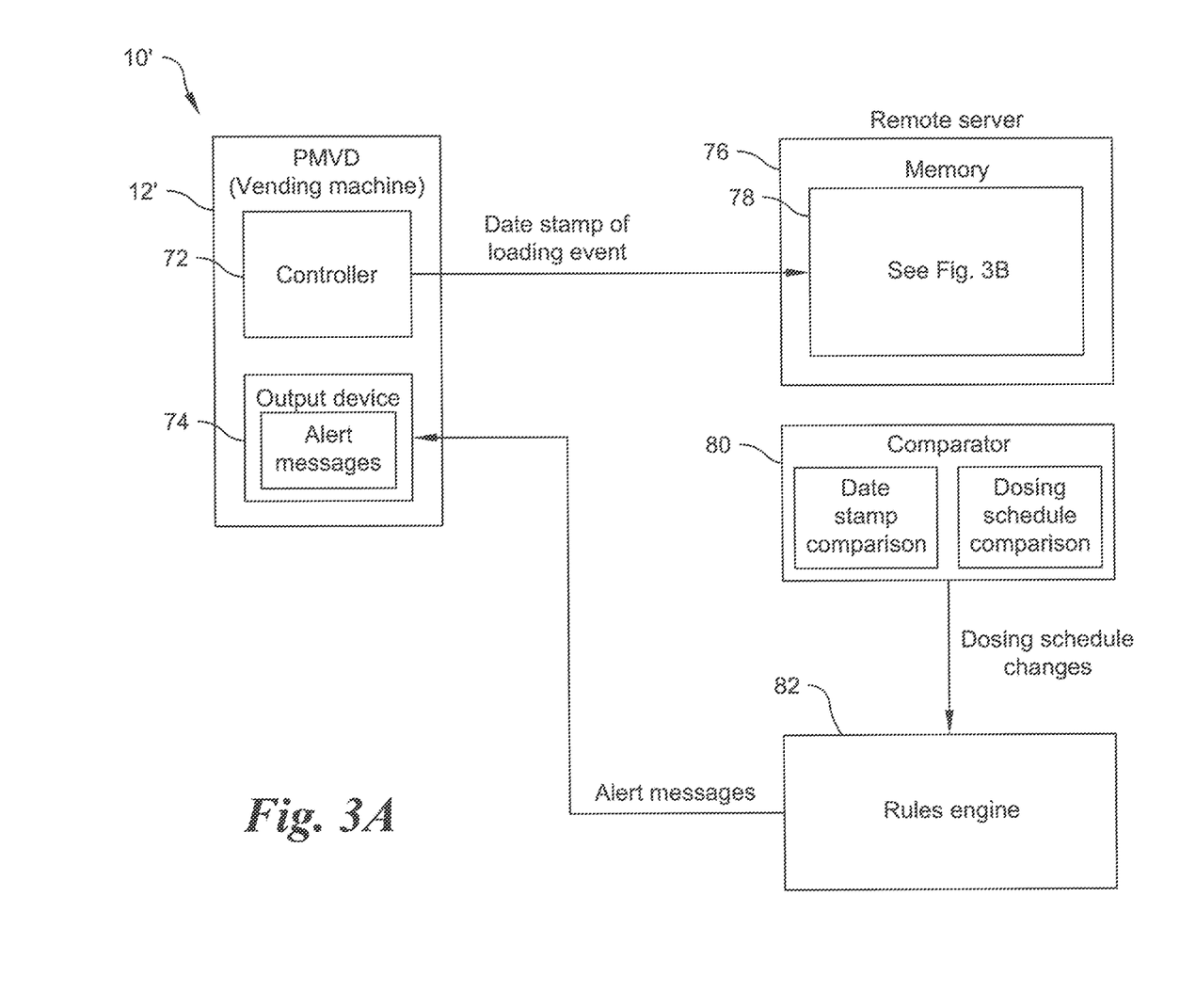
FIGS. 3A and 3B, taken together, is a schematic diagram of additional elements of the system of FIG. 1A, in accordance with another preferred embodiment of the present invention.
Figure 3D:
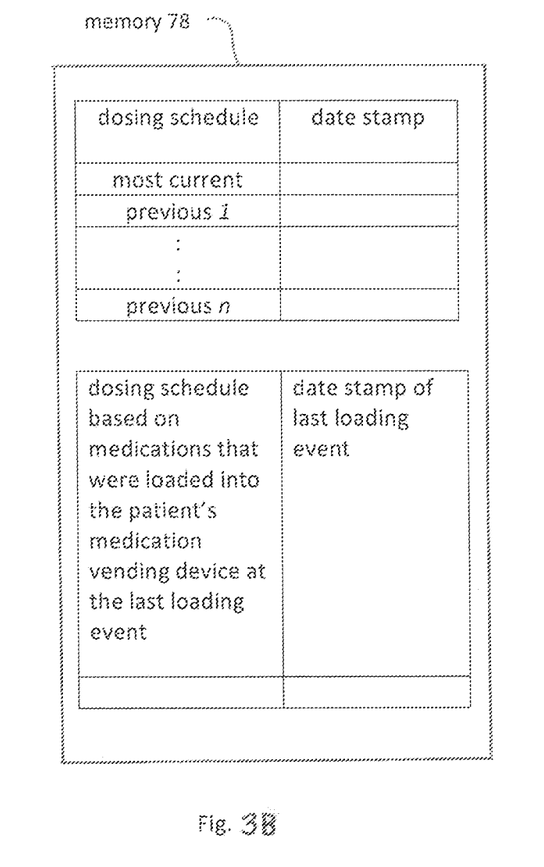

FIGS. 3A and 3B. taken together, is a schematic diagram of additional elements of the system 10 (referred to as system 10') in accordance with another preferred embodiment of the present invention. This embodiment does not make use of the external scanner 66, electronic translator 68, or comparator 70 of FIGS. 1A and 1B, but relies on many of the other elements of FIG. 1A.

Referring to FIG. 3A, the medication vending device 12 (referred to as medication vending device 12') further includes controller 72 and output device 74. The output device 74 may include the display shown in the medication vending device 12 of FIG. 1A. The system 10' further includes remote server 76 which contains memory 78 (the contents of which are shown in FIG. 3B), comparator 80, and rules engine 82. These elements are described in more detail below.

In contrast to the previously described embodiment which addresses pre-loading prescription changes, the embodiment of FIGS. 3A and 3B addresses post-loading prescription changes, meaning that medication packages loaded into the medication vending device 12' were correct for the most current dosing schedule on the date of loading, but medication changes subsequently occurred.

Referring to the combination of FIGS. 1A-1F, 3A, and 3B, the system 10' provides an apparatus for ensuring compliance with a medication dosing schedule. The dosing schedule is associated with a specific patient and includes one or more dosing times per day. The medication is delivered to the patient via medication packages that are intended to match the dosing schedule.

The system 10' includes a medication vending device 12' configured to vend the medication packages previously loaded therein. The medication vending device 12' includes the controller 72 and the output device 74 discussed above. The controller 72 is configured to operate the medication vending device 12'. The controller 72 generates an electronic message whenever medication packages are loaded into the medication vending device 12'. The electronic message includes a date stamp of the loading time. The output device 74 communicates alert messages regarding the medication to the patient, as will be discussed in more detail below.

The system 10' further include the remote server 76 which is in electronic communication with the controller 72 to receive the electronic message. The remote server 76 includes the memory 78 that stores the patient's dosing schedule. More specifically, the memory 78 stores at least the following data, as shown in FIG. 3B:

1. The patient's most current dosing schedule, and a date stamp of when the most current dosing schedule was stored in the memory 78.

2. One or more previous dosing schedules, and a date stamp of when the respective previous dosing schedules were stored in the memory.

3. The date stamp of the last loading event for the patient's medication vending device. The date stamp is continuously updated with each loading event. The date stamp of previous loading events may be kept for archival purposes, if desired.

The system 10' further includes the comparator 80 which is in electronic communication with the memory 78 of the remote server 76. The comparator is configured to perform at least the following functions:

1. Compare the date stamp of the patient's most current dosing schedule with the date stamp of the last loading event for the patient's medication vending device 12', and identify a potential alert condition when the date stamp of the patient's most current dosing schedule is later in time than the date stamp of the last loading event for the patient's medication vending device 12'.

2. When the potential alert condition occurs, compare the patient's most current dosing schedule with the patient's dosing schedule that matches the medications that were loaded into the patient's medication vending device 12' at the last loading event, and identify all changes therebetween. Presumably, the latter dosing schedule is the same dosing schedule that existed at the time of the last loading event. That is, the presumption is that the medication packages loaded into the medication vending machine 12' were for the most current dosing schedule on the date of loading. However, since this presumption might not always be correct, which is what the first embodiment in FIGS. 1A-1F addresses, the safest approach is to store the patient's dosing schedule that matches the medications that were actually loaded into the patient's medication vending device 12' at the last loading event.

3. Output the identified changes.

The system 10' further includes the rules engine 82 that receives the identified changes and determines from the identified changes and rules of the rules engine 82 whether an alert message should be generated and electronically communicated to the patient's medication vending device 12', and what the alert message should be. The output device 74 of the patient's medication vending device 12' is configured to communicate the alert message to the patient.

Examples of rules of the rules engine 82 include the following:

1. Generate an alert message when all of the medications in the medication packages for a particular dosing time have been discontinued. In this scenario, the alert message sent to the output device 74 of the patient's medication vending device 12' is a message that the medication package for the respective dosing time will not be vended and should be skipped, or that none of the medication in the medication package for the respective dosing time should be taken by the patient, even if vended.

2. Generate an alert message when one or more, but not all, of the medications in the medication packages for a respective dosing time were discontinued. In this scenario, the alert message sent to the output device 74 of the patient's medication vending device 12' is a message that the patient should not take any of the discontinued medications. In one embodiment of this scenario, the output device 74 may include a display, and an image of each of the discontinued medications is shown on the display, in addition to the message alerting the patient not to consume any of the discontinued medications.

3. No alert message is generated when the identified change is only a change in medication dosage level of an existing medication in the dosing schedule. For example, it may be determined that dosage level changes are less critical to address in the short-term than discontinued medications, and it may be acceptable from a medical standpoint to simply wait until the next loading cycle to vend medications having the updated dosage level. The rules for when to select the "no alert" message option may further be programmed on a medication by medication basis (i.e., this option is permitted for some medications, but not for others).

4. No alert message is generated when the identified change is only an addition of a new medication to the dosing schedule. Again, it may be acceptable from a medical standpoint to simply wait until the next loading cycle to add a new medication to the vended medications.

5. In an alternative embodiment of the "no alert" rule, the rule may be to generate an information-only message noting the dosage change or newly added medication, but that the existing medications should still be taken, and new medication packages will be loaded into the medication vending machine 12' shortly that will reflect the medication changes.

The remote server 76, comparator 80, and rules engine 82 may all be remote from the medication vending device 12' and in communication therewith via the electronic network 28. Any one of these elements (remote server 76, comparator 80, and rules engine 82) may be part of the host site 14, or may be separately located from the host site 14. While the explanation above refers to actions taken with respect to only one medication vending device 12', it should be understood that the actions described above occur for multiple medication vending devices 12, as shown in FIG. 1A. Since each medication vending device 12 and each dosing schedule is associated with a particular patient, the computer elements simply need to ensure that any comparisons that are being performed relate to the same patient.

The present invention may be implemented with any combination of hardware and software. When implemented in software, the software code for the electronic translator 68, comparator 70, controller 72, remote server 76, comparator 80, and rules engine 82 can be executed on any suitable processor or collection of processors, whether provided in a single computer or distributed among multiple computers.

The electronic translator 68, comparator 70, controller 72, remote server 76, comparator 80, and rules engine 82 are not a general-purpose computers, but instead are specialized computer machines that perform a myriad of functions that are not native to a general-purpose computer, absent the addition of specialized programming.

Preferred embodiments of the present invention may be implemented as methods, of which examples have been provided. The acts performed as part of the methods may be ordered in any suitable way. Accordingly, embodiments may be constructed in which acts are performed in an order different than illustrated, which may include performing some acts simultaneously, even though such acts are shown as being sequentially performed in illustrative embodiments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. An apparatus for ensuring compliance with a medication dosing schedule, the dosing schedule being associated with a specific patient and including one or more dosing times per day, wherein the medication is delivered to the patient via medication packages that are intended to match the dosing schedule, each medication package including a machine-readable code printed thereon that is usable to identify (i) contents of the medication package, and (ii) a specific patient that the medication in the medication package was previously prescribed for, the apparatus including:
   (a) a memory that stores the patient's dosing schedule, the dosing schedule including a patient identifier;
   (b) a medication vending device configured to vend the medication packages previously loaded therein, the medication vending device including:
      (i) an identifier corresponding to a specific patient that the medication vending device is assigned to, and
      (ii) a scanner configured to read the machine-readable code printed on selected ones of the medication packages prior to loading the medication packages into the medication vending device;
   (c) an electronic translator configured to receive and process the scanned machine-readable code and output
      (i) contents of the scanned medication packages, and
      (ii) the specific patient that the medication in the medication packages was previously prescribed for; and
   (d) a comparator in electronic communication with (i) the memory that stores the patient's dosing schedule, (ii) the medication vending device, and (iii) the output of the electronic translator, the comparator being configured to:
      (i) compare the patient's dosing schedule with the output of the electronic translator to identify any discrepancies between (A) the patient's dosing schedule and the contents of the scanned medication packages as outputted by the electronic translator, and (B) the patient identifier in the dosing schedule and the specific patient that the medication in the scanned medication packages was previously prescribed for as outputted by the electronic translator, and
      (ii) compare the identifier of the medication vending device with one or more of (A) the specific patient that the medication in the scanned medication packages was previously prescribed for, and (B) the patient identifier in the dosing schedule, and
      (iii) output a message indicating any discrepancies identified in the comparisons,
   wherein the medication vending device is in electronic communication with the comparator, and is configured to output the message indicating any discrepancies identified in the comparisons,
   wherein the message provides an alert to either (i) inhibit a person from loading selected ones of the medication packages into the medication vending device, or (ii) communicate a change in the patient's dosing schedule so that appropriate action can be taken when the loaded medication packages are subsequently vended.

2. The apparatus of claim 1 wherein the machine-readable code is a two-dimensional code.

3. The apparatus of claim 2 wherein the two-dimensional code is a QR code.

4. The apparatus of claim 1 wherein the scanner is configured to read the machine-readable code printed on one medication package for each dosing time per day, and wherein the comparison is made between the dosing schedule and the contents of the scanned medication packages for each of the dosing times per day.

5. The apparatus of claim 1 wherein the comparator is part of the medication vending device.

6. The apparatus of claim 1 wherein the memory that stores the dosing schedule is located in a medication administration computer remotely located from the medication vending device, and wherein the medication administration computer maintains an electronic record for a plurality of patients, each electronic record having an associated patient identifier.

7. The apparatus of claim 1 wherein the medication vending device further includes:
   (iii) an operating system;
   (iv) one or more application software programs executed using the operating system, wherein one of the application software programs is a scanner application, and
   (iv) a camera accessible by the scanner application,
   wherein the scanner is implemented using the camera and the scanner application.

8. The apparatus of claim 1 wherein the patient's dosing schedule is stored in a remotely located server, and the memory is located in the medication vending device, and wherein the medication vending device is in electronic communication with the remotely located server to allow the patient's dosing schedule to be downloaded into the memory.

9. An apparatus for ensuring compliance with a medication dosing schedule, the dosing schedule being associated with a specific patient and including one or more dosing times per day, wherein the medication is delivered to the patient via medication packages that are intended to match the dosing schedule, each medication package including a machine-readable code printed thereon that is usable to identify (i) an order identifier (ID) of the medication package, the apparatus including:
- (a) a memory that stores the order ID's of the medication packages, each order ID being associated with a respective patient identifier, wherein a new order ID is created whenever a change is made to the patient's dosing schedule;
- (b) a medication vending device configured to vend the medication packages previously loaded therein, the medication vending device including:
  - (i) an identifier corresponding to a specific patient that the medication vending device is assigned to, and
  - (ii) a scanner configured to read the machine-readable code printed on selected ones of the medication packages prior to loading the medication packages into the medication vending device;
- (c) an electronic translator configured to receive and process the scanned machine-readable code and output the order ID; and
- (d) a comparator in electronic communication with (i) the memory that stores the order ID's, (ii) the medication vending device, and (iii) the output of the electronic translator, the comparator being configured to:
  - (i) compare the order ID as outputted by the electronic translator with the most recent order ID in the memory for the respective patient, wherein a discrepancy occurs when the order ID as outputted by the electronic translator is not the most recent order ID in the memory for the respective patient, and
  - (ii) compare the identifier of the medication vending device with the patient identifier associated with the order ID as outputted by the electronic translator, and
  - (iii) output a message indicating any discrepancies identified in the comparisons,
  wherein the medication vending device is in electronic communication with the comparator, and is configured to output the message indicating any discrepancies identified in the comparisons,
  wherein the message provides an alert to inhibit a person from loading selected ones of the medication packages into the medication vending device.

10. The apparatus of claim 9 wherein the machine-readable code is a two-dimensional code.

11. The apparatus of claim 10 wherein the two-dimensional code is a QR code.

12. The apparatus of claim 9 wherein a different order ID is created for each dosing time per day, and wherein the scanner is configured to read the machine-readable code printed on one medication package for each dosing time per day, and wherein the comparison is made between the order IDs for each of the dosing times as outputted by the electronic translator with the most recent order IDs in the memory for the respective patient for each of the dosing times, wherein a discrepancy occurs when any of the order ID's as outputted by the electronic translator is not the most recent order ID in the memory for the respective patient and for the respective dosing time.

13. The apparatus of claim 9 wherein the comparator is part of the medication vending device.

14. The apparatus of claim 9 wherein the memory that stores the order ID's is located in a medication administration computer remotely located from the medication vending device, and wherein the medication administration computer maintains an electronic record for a plurality of patients, each electronic record having an associated patient identifier.

15. The apparatus of claim 9 wherein the medication vending device further includes:
- (iii) an operating system;
- (iv) one or more application software programs executed using the operating system, wherein one of the application software programs is a scanner application, and
- (iv) a camera accessible by the scanner application,
wherein the scanner is implemented using the camera and the scanner application.

16. The apparatus of claim 9 wherein the machine-readable code is an encoded order ID, and thus is directly usable to identify the order ID.

17. An apparatus for ensuring compliance with a medication dosing schedule, the dosing schedule being associated with a specific patient and including one or more dosing times per day, wherein the medication is delivered to the patient via medication packages that are intended to match the dosing schedule, the apparatus comprising:
- (a) a medication vending device configured to vend the medication packages previously loaded therein, the medication vending device including:
  - (i) a controller configured to operate the medication vending device, wherein the controller generates an electronic message whenever medication packages are loaded into the medication vending device, the electronic message including a date stamp of the loading time, and
  - (ii) an output device for communicating alert messages regarding the medication to the patient;
- (b) a remote server in electronic communication with the controller to receive the electronic message, the remote server including a memory that stores the patient's dosing schedule, the memory storing:
  - (i) the patient's most current dosing schedule, and a date stamp of when the most current dosing schedule was stored in the memory,
  - (ii) one or more previous dosing schedules, and a date stamp of when the respective previous dosing schedules were stored in the memory, and
  - (iii) the date stamp of the last loading event for the patient's medication vending device;
- (c) a comparator in electronic communication with the memory of the remote server, the comparator configured to:
  - (i) compare the date stamp of the patient's most current dosing schedule with the date stamp of the last loading event for the patient's medication vending device, and identify a potential alert condition when the date stamp of the patient's most current dosing schedule is later in time than the date stamp of the last loading event for the patient's medication vending device,
  - (ii) when the potential alert condition occurs, compare the patient's most current dosing schedule with the patient's dosing schedule that matches the medications that were loaded into the patient's medication vending device at the last loading event, and identify all changes therebetween, and
  - (iii) output the identified changes; and
- (d) a rules engine that receives the identified changes and determines from the identified changes and rules of the rules engine whether an alert message should be generated and electronically communicated to the patient's medication vending device, and what the alert message should be, wherein the output device of the patient's medication vending device is configured to communicate the alert message to the patient.

18. The apparatus of claim 17 wherein one of the rules of the rules engine is to generate an alert message when one or more, but not all, of the medications in the medication packages for a respective dosing time were discontinued, and the alert message sent to the output device of the patient's medication vending device is a message that the patient should not take any of the discontinued medications.

19. The apparatus of claim 18 wherein the output device includes a display, and an image of each of the discontinued medications is shown on the display, in addition to the message alerting the patient not to consume any of the discontinued medications.

20. The apparatus of claim 17 wherein one of the rules of the rules engine is to generate an alert message when all of the medications in the medication packages for a particular dosing time have been discontinued, and the alert message sent to the output device of the patient's medication vending device is a message that the medication package for the respective dosing time will not be vended and should be skipped, or that none of the medication in the medication package for the respective dosing time should be taken by the patient, even if vended.

21. The apparatus of claim 17 wherein one of the rules of the rules engine is that no alert message is generated when the identified change is only a change in medication dosage level of an existing medication in the dosing schedule.

22. The apparatus of claim 17 wherein one of the rules of the rules engine is that no alert message is generated when the identified change is only an addition of a new medication to the dosing schedule.

* * * * *